United States Patent [19]

Sawada et al.

[11] Patent Number: 5,843,908
[45] Date of Patent: Dec. 1, 1998

[54] PRADIMICINS L AND FL, AND DERIVATIVES THEREOF

[75] Inventors: Yosuke Sawada, Tokyo; Kyoichiro Saitoh, Zushi; Masami Hatori, Yokosuka; Takeo Miyaki; Toshikazu Oki, both of Yokohama; Koji Tomita, Tokyo, all of Japan

[73] Assignee: Bristol-Myers Squibb Company, New York, N.Y.

[21] Appl. No.: 589,728

[22] Filed: Sep. 28, 1990

[51] Int. Cl.⁶ .......................... A61K 31/70; C07H 15/24
[52] U.S. Cl. ................... 514/27; 514/25; 536/6.4; 536/16.8; 536/18.1
[58] Field of Search ................... 536/18.1, 16.8, 536/6.4; 514/27

[56] References Cited

U.S. PATENT DOCUMENTS

| | | | |
|---|---|---|---|
| 4,130,709 | 12/1978 | Nagarajan | 536/16.8 |
| 4,870,165 | 9/1989 | Oki et al. | 536/6.4 |
| 4,960,755 | 10/1990 | Nishio et al. | 514/8 |
| 4,973,673 | 11/1990 | Sawada et al. | 536/18.1 |

*Primary Examiner*—Elli Peselev
*Attorney, Agent, or Firm*—Thomas R. Savitsky

[57] ABSTRACT

The present invention relates to novel antifungal antibiotics herein designated as pradimicin L and pradimicin FL, and derivatives thereof. Pradimicins L and FL are produced by *Actinomadura verrucosospora* subsp. *neohibisca* strain R103-3, ATCC No. 53930.

10 Claims, No Drawings

PRADIMICINS L AND FL, AND DERIVATIVES THEREOF

BACKGROUND OF THE INVENTION

1. Field of the Invention

The present invention relates to novel antifungal compounds, process for their production, their therapeutic use, and pharmaceutical compositions containing them. The invention also relates to the antibiotic producing microorganism. More particularly, the novel compounds of this invention belong to the family of pradimicin antibiotics.

2. Background Art

Pradimicins, formerly called BU-3608 antibiotics, are a family of broad spectrum antibiotics active against pathogenic yeasts and fungi. A number of pradimicin compounds obtained by fermentation of *Actinomadura hibisca* have been reported, and their structures are shown below as formula (I):

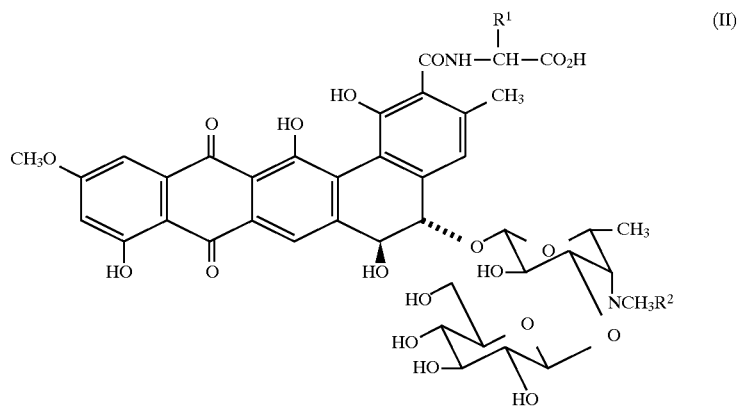

| Pradimicin | $R^a$ | $R^b$ | $R^c$ |
|---|---|---|---|
| A | $CH_3$ | $CH_3$ | β-D-Xylosyl |
| B | $CH_3$ | $CH_3$ | H |
| C | $CH_3$ | H | β-D-Xylosyl |
| D | H | $CH_3$ | β-D-Xylosyl |
| E | H | H | β-D-Xyiosyl |
| FA-1 | $CH_2OH$ | $CH_3$ | β-D-Xylosyl |
| FA-2 | $CH_2OH$ | H | β-D-Xylosyl |

U.S. Pat. No. 4,870,165 discloses pradimicins A, B, and C. Pradimicin C is identical to benanomicin B disclosed in European Patent Application No. 315,147 (published May 10, 1989).

European Patent Application No. 345,735 (published Dec. 13, 1989) discloses pradimicins D, E, and their respective desxylosyl derivatives.

European Patent Application No. 351,799 (published Jan. 24, 1990) discloses N-alkylated derivatives of pradimicins A, B, C, D, and E.

European Patent Application No. 368,349 (published May 16, 1990) discloses pradimicins FA-1, FA-2, their respective desxylosyl derivatives, and N-alkylated derivatives thereof.

It will be noted that heretofore reported pradimicins possess either a monosaccharide moiety (in formula I, the amino sugar in which $R^c$ is hydrogen) or a disaccharide moiety consisting of the amino sugar and β-D-xylose linked thereto. Surprisingly, it has now been discovered that a new subspecies of *Actinomadura verrucosospora* is capable of producing pradimicin antibiotics in which the D-xylose group has been replaced by D-glucose. This discovery, thus, forms the basis of the instant application.

SUMMARY OF THE INVENTION

The present invention provides novel compounds of formula (II)

wherein $R^1$ is methyl or hydroxymethyl, and the resulting amino acid has the D-configuration; and $R^2$ is hydrogen or $C_{1-5}$ alkyl; or a pharmaceutically acceptable salt thereof.

A further aspect of the invention provides a biologically pure culture of *Actinomadura verrucosospora* subsp. *neohibisca*.

Yet another aspect of the invention provides a process for preparing a compound having formula (III)

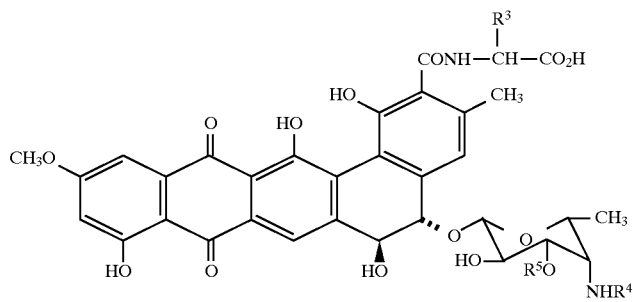

(III)

wherein $R^3$ is hydrogen, $R^4$ is hydrogen or methyl, and $R^5$ is β-D-xylosyl; or $R^3$ is methyl and the resulting alanyl residue has the D-configuration, $R^4$ is hydrogen or methyl, and $R^5$ is hydrogen, β-D-xylosyl, or β-D-glucosyl; which comprises cultivating an antibiotic-producing strain of *Actinomadura verrucosospora* subsp. *neohibisca* under submerged and aerobic conditions in a medium containing assimilable carbon and nitrogen sources.

Yet another aspect of the present invention provides a process for preparing a compound having formula (IV)

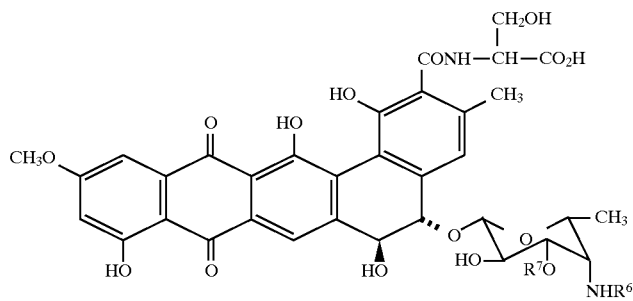

(IV)

wherein $R^6$ is hydrogen or methyl, and $R^7$ is β-D-xylosyl; or $R^6$ is methyl and $R^7$ is β-D-glucosyl; which comprises cultivating an antibiotic-producing strain of *Actinomadura verrucosospora* subsp. *neohibisca* under submerged and aerobic conditions in a medium containing assimilable sources of carbon, nitrogen, and D-serine.

Yet a further aspect of the present invention provides a method for treating fungal infections which comprises administering to a host so afflicted an antifungal effective amount of a compound of formula (I).

A further aspect of the invention provides a pharmaceutical composition comprising a compound of formula (I) and a pharmaceutically acceptable carrier.

DETAILED DESCRIPTION OF THE INVENTION

One aspect of the present invention provides antibiotics of formula (II) and pharmaceutically acceptable salts thereof. The compounds of formula (II) may be divided into subsets; one such subset provides two pradimicin antibiotics herein designated as pradimicin L and pradimicin FL which are produced by fermentation of *Actinomadura verrucosospora* subsp. *neohibisca*. The structures of pradimicin L and pradimicin FL are shown below as formulas (Va) and (Vb), respectively.

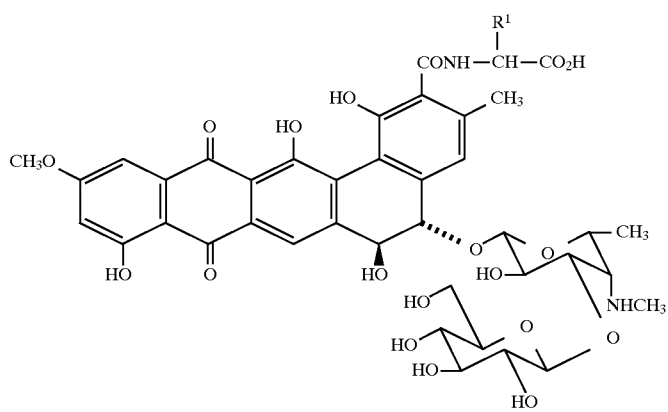

pradimicin L (Va): R¹ = methyl
pradimicin FL (Vb): R¹ = hydroxymethyl

As can be seen, pradimicin L possesses a D-alanine group whereas pradimicin FL has a D-serine group.

Another subset of compounds of formula (II) are N-alkylated derivatives of pradimicin L and pradimicin FL which may be prepared from the respective parent compounds by known chemical methods such as reductive alkylation.

As used herein, unless otherwise specified, the term "alkyl" encompasses straight and branched carbon chains. "Pharmaceutically acceptable salt" includes acid addition salts formed with inorganic acids such as hydrochloric acid, sulfuric acid, phosphoric acid, nitric acid and the like, or with organic acids such as acetic acid, citric acid, fumaric acid, lactic acid, tartaric acid and the like; base salts formed with inorganic bases such as sodium hydroxide, potassium hydroxide, sodium carbonate, calcium carbonate, magnesium hydroxide and the like, or with organic bases such as diethylamine, ethylenediamine, triethylamine, ethanolamine and the like; and internal salt providing the zwitterion. The abbreviation "CBZ" is used to designate the benzyloxycarbonyl radical.

1. Preparation of Pradimicin L and Pradimicn FL

Pradimicin L is produced by cultivating an antibiotic-producing strain of *Actinomadura verrucosospora* subsp. *neohibisca,* or a variant thereof, or a mutant thereof, in a medium containing sources of assimilable carbon and nitrogen. Pradimicin FL is similarly produced when the medium contains, in addition, an assimilable source of D-serine.

Pradimicin L may be produced by *Actinomadura verrucosospora* subsp. *neohibisca* strain R103-3 and a mutant strain derived therefrom designated as strain A10019. Strain R103-3 also produces pradimicin FL in media containing an assimilable source of D-serine. The characterizing properties of strains R103-3 and A10019 are described hereinbelow.

A. Producing Organism (i) Strain R103-3 was isolated from a soil sample collected in Puerto Viejo Costa, Peru. A biologically pure culture of strain R103-3 was deposited with the American Type Culture Collection, 12301 Parklawn Drive, Rockville, Md. under accession number ATCC 53930. This culture has been accepted for deposit under the BUDAPEST TREATY ON THE INTERNATIONAL RECOGNITION OF THE DEPOSIT OF MICROORGANISMS FOR THE PURPOSES OF PATENT PROCEDURE.

The morphological, cultural, physiological, and chemotaxonomical characteristics of strain R103-3 are similar to those of *Actinomadura verrucosospora,* but strain R103-3 is differentiated from *Actinomadura verrucosospora* in the formation of red diffusible pigments and other physiological characteristics. Therefore, strain R103-3 was designated *Actinomadura verrucosospora* subsp. *neohibisca* subsp. nov.

(a) Morphology

Strain R103-3 forms short or rudimental aerial mycelium and well-branched non-fragmentary substrate mycelium. Loop or spiral short spore-chains (5–12 spores per chain) are formed on the aerial hyphae. The spores are oval (0.8× 1.2–1.5 μm), non-motile, and have a warty surface.

(b) Cultural and Physiological Characteristics

The cultural and physiological characteristics were examined by the methods of Shirling and Gottlieb (*Int. J. Syst. Bacteriol.,* 1966, 16:313–340), and Gordon, et al. (*J. Gen. Microbiol.,* 1978, 109:69–78).

Strain R103-3 forms aerial mycelium and spore-chain in ISP media Nos. 3, 4, 5, and 7 and produces abundantly reddish diffusible pigments (pradimicins) in Czapek's agar and natural organic media, such as ISP medium No. 2. Cultural and physiological characteristics are shown in Tables 1 and 2, respectively.

TABLE 1

Cultural Characteristics of Strain R103-3

| Medium | Growth | Aerial Mycelium | Substrate Mycelium | Diffusible Pigment |
|---|---|---|---|---|
| Sucrose-nitrate agar (Czapek-Dox agar) | Moderate | None | Very deep red (14) | Very deep purplish red (257) |
| Tryptone-yeast extract broth (ISP No. 1) | Poor, not turbid | None | Deep red (13) | Moderate red (15) |
| Yeast extract-malt extract agar (ISP No. 2) | Good | None | Very deep red (14) | Very dark red (17) |
| Oatmeal agar (ISP No. 3) | Moderate | Moderate; pale pink (7) | Moderate pink (5) | Grayish pink (8) to light grayish red (18) |
| Inorganic salts-starch agar (ISP No. 4) | Moderate | Poor; white | Moderate pink (5) | Light grayish red (18) |
| Glycerol-asparagine | Poor | Poor; white | Colorless | None |

TABLE 1-continued

Cultural Characteristics of Strain R103-3

| Medium | Growth | Aerial Mycelium | Substrate Mycelium | Diffusible Pigment |
|---|---|---|---|---|
| agar (ISP No. 5) Peptone-yeast extract-iron agar (ISP No. 6) | Good | Scant; white | Grayish pink (8) to deep red (13) | Very deep red (14) |
| Tyrosine agar (ISP No. 7) | Moderate | Poor; white | Moderate red (15) | Light yellowish pink (28) |
| Glucose-asparagine agar | Poor | None | Colorless | Light pink (4) |
| Nutrient agar | Moderate | Poor; white | Dark pink (6) | Dark red (16) |
| Bennett's agar | Good | None | Blackish red (21) | Blackish red (21) |

Observation after incubation at 28° for 3 weeks.
Color Name: ISCC-NBS color-name charts.

TABLE 2

Physiological Characteristics of Strain R103-3

| Decomposition of: | | Acid Production from*: | |
|---|---|---|---|
| Adenine | − | Adonitol | − |
| Casein | + | D-Arabinose | − |
| Hippuric acid | + | L-Arabinose | + |
| Hypoxanthine | − | Cellobiose | + |
| Tyrosine | + | Dulcitol | − |
| Xanthine | − | Erythritol | − |
| Decarboxylation of: | | D-Fructose | + |
| Benzoate | − | D-Galactose | − |
| Citrate | − | D-Glucose | + |
| Mucate | − | Glycerol | − |
| Succinate | + | Inositol | − |
| Tartrate | − | Lactose | − |
| Production of: | | D-Mannitol | + |
| Amylase | − | D-Mannose | − |
| Esculinase | + | D-Melezitose | − |
| Gelatinase | + | Melibiose | − |
| Nitrate reductase | + | Methyl-α-glucoside | − |
| Tyrosinase | − | Raffinose | − |
| Urease | − | L-Rhamnose | + |
| Growth in: | | D-Ribose | + |
| Lysozyme, 0.001% | − | Salicine | + |
| NaCl, 1%–7% | + | Soluble starch | + |
| 8% | − | D-Sorbitol | − |
| pH, 5.8–11.0 | + | L-Sorbose | − |
| 25° C.–39° C. | + | Sucrose | + |
| 22° C. and 42° C. | − | Trehalose | − |
| | | D-Xylose | + |

*Basal Medium: Pridham-Gottlieb medium (ISP No. 9), omitted CuSO$_4$.7H$_2$O (c) Chemotaxonomy The whole cell hydrolyzate of strain R103-3 contains meso-diaminopimelic acid, glucose, and madurose. Hence, the strain belongs to cell wall type III and sugar pattern B. The phospholipids contain phosphatidylglycerol and phosphatidylinositol without nitrogenous phospholipids and, hence, is placed in type P-I.

(d) Taxonomic Position

Based on the morphology and chemotaxonomy of strain R103-3, the strain is placed in the genus Actinomadura. Among hitherto described known species of Actinomadura, strain R103-3 is physiologically most similar to *Actinomadura verrucosospora*, but it is differentiated from the latter in its production of red diffusible pigment, resistance to NaCl, and negative acid formation from glycerol, lactose, and trehalose. Thus, strain R103-3 was designated *Actinomadura verrucosospora* subsp. *neohibisca* subsp. nov.

Strain R103-3 is also distinct from *Actinomadura hibisca*, known producer of pradimicins. Table 3 shows the differential characteristics of *Actinomadura hibisca* strain P157-2 (ATCC No. 53557) and strain R103-3.

TABLE 3

Differential Characteristics of *Actinomadura verrucosospora* Subsp. *neohibisca* Strain R103-3 from *Actinomadura hibisca* Strain P157-2

| | Strain R103-3 | Strain P157-2 |
|---|---|---|
| Morphology: | | |
| Spore chain | Short, hook | Long, straight |
| Spore surface | Warty | Smooth |
| Cultural and physiological characteristics: | | |
| Tyrosine agar: | | |
| Brownish pigment | Not Formed | Forined |
| Glucose-asparagine agar: | | |
| Growth | Poor | Abundant |
| Reddish pigment | Scant | Abundant |
| Utilization of: | | |
| L-Arabinose | + | − |
| D-Mannitol | + | − |
| L-Rhamnose | + | − |
| D-Xylose | + | − |

(ii) Strain A10019 is derived from strain R103-3 by mutation using N'-methyl-N'-nitro-N-nitrosoguanidine (NTG). A biologically pure culture of A10019 was deposited with the American Type Culture Collection under accession number ATCC 55091. This culture has been accepted for deposit under the BUDAPEST TREATY ON THE INTERNATIONAL RECOGNITION OF THE DEPOSIT OF MICROORGANISMS FOR THE PURPOSES OF PATENT PROCEDURE. The procedure for mutation of strain R103-3 and for the screening of the mutant strains is described below.

Strain R103-3 was grown at 28° C. for 14 days on a modified Bennett's agar consisting of soluble starch 0.5%, glucose 0.5%, fish meat extract 0.1%, yeast extract 0.1%, NZ-case 0.2%, NaCl 0.2%, CaCO$_3$ 0.1%, and agar 1.6%; pH 7.0. Spores of the strain were suspended in saline, dispersed by sonication for 20 seconds in ice-bath, harvested by centrifugation at 3,500 rpm for 10 minutes at 25° C., and resuspended in 10 mM Tris-HCl, pH 9.0. The spore suspension (3 ml) was mixed with 3 ml of NTG solution (5,000 μg/ml in a mixture of water-dimethyl sulfoxide 9:1 (v/v)). The mixture was gently shaken at 28° C. for 1 hour. The NTG-treated spores were harvested by centrifugation, resuspended in saline, spread on a new agar plate, and incubated at 28° C. for 7 days. Each colony was picked up, inoculated to a fresh agar plate, and incubated at 28° C. for 7 days to be used as a mother culture plate. Each culture was transferred to 10 ml of the vegetative medium (Medium A) consisting of Na L-glutamate 0.1%, L-methionine 0.05%, L-arginine 0.05%, soluble starch 1.0%, glucose 1.0%, (NH$_4$)$_2$ SO$_4$ 0.01%, K$_2$HPO$_4$ 0.6%, MgSO$_4$.7H$_2$O 0.05%, NaCl 0.05%, CaCO$_3$ 0.3%, salt solution (FeSO$_4$.7H$_2$O 0.1 g, ZnSO$_4$.7H$_2$O 0.1 g, MnCl$_2$.4H$_2$O 0.1 g, in 1 liter of water) 1% v/v, pH 7.0. The culture was incubated at 28° C. for 14 days on a shaker operating at 200 rpm. Pradimicin L produced in each fermentation broth was analyzed by silica gel TLC (Merck Co., Kieselgel 60 $F_{254}$) using a solvent system of methyl-acetate-n-propanol-28% ammonia (3:7:4) and HPLC (Waters M600, YMC-A301-3) using a solvent system of 0.15% (w/v) potassium phosphate buffer (pH 3.5) and acetonitrile (3:1) detecting at 254 nm. Samples for HPLC were prepared as follows: The fermentation broth was centrifuged at 10,000 rpm for 5 minutes, and the supernatant was adjusted pH to 2.0 with dil. HCl and centrifuged again. The supernatant was adjusted pH to 5.0 with dil. NaOH and centrifuged. The sediment obtained was dissolved in water at pH 3.5 and passed through a Sep-Pak® (Millipore-Waters) by diluting with acetonitrile-0.15% potassium phosphate buffer (pH 3.5) (1:1). The filtrate was mixed with DMSO (1:1) and filtered again through a Millipore Filter HVA (0.45 $\mu$m). As a result, a mutant A10019 was selected as the producing organism for larger-scale fermentation of pradimicin L based on its ability to produce more pradimicin L in comparison with that of pradimicins A and C.

| Strain | Medium | Total Production* ($\mu$g/ml) | Ratio (%) of pradimicin** | | | | | |
|---|---|---|---|---|---|---|---|---|
| | | | A | B | C | D | E | L |
| R103-3 (Parent) | A | 290 | 58 | 6 | 22 | 2 | 1 | 11 |
| A10019 (Mutant) | A | 310 | 57 | 1 | 8 | 3 | 1 | 30 |

*Determination of pradimicin components. The fermentation broth was centrifuged at 10,000 rpm for 10 minutes. The supernatant was diluted with 0.01N NaOH—MeOH (1:1) and its optical density measured at 500 nm. Antibiotic concentration was expressed as amount of BU-3608 A free base. Data from the fermentation broths of 11 days.
**Determined by HPLC (Waters M600, YMC-A301-3 system) using a 3:1 mixture of 0.15% potassium phosphate-buffer acetonitrile (pH 3.5) as solvent, with UV detection at 254 nm.

Differential characteristics between strain R103-3 and A10019 are shown in Table 4. There is no distinct difference in sugar utilization between the two cultures.

TABLE 4

Differential Characteristics of Strain R103-3 and Its Mutant No. A10019

| Cultural Characteristics | | Strain R103-3 | No. A10019 |
|---|---|---|---|
| Sucrose-nitrate agar | G | Moderate | None |
| | AM | None | None |
| | R | Very deep purple red (14) | Moderate pink (5) |
| | DP | Very deep red (257) | Deep purplish red (256) |
| Tyrosine agar (ISP No. 7) | G | Moderate | Poor |
| | AM | Poor; white | Very scant |
| | R | Moderate red (15) | Moderate pink (5) |
| | DP | Light yellowish pink (28) | Moderate pink (5) |
| Papavizas' V-8 agar | G | Good | Good |
| | AM | Scant; white | None |
| | R | Very deep red (14) | Dark red (16) |
| | DP | Very deep red (14) | Very dark red (17) |

Observation after incubation at 28° C. for 3 weeks.
G: growth; AM: aerial mycelium; R: reverse color; DP: diffusible pigment.

B. Antibiotic Production

Strain R103-3 produces the novel antibiotic pradimicin L, along with the known pradimicins A, B, C, D, and E, when cultivated in a conventional medium. The organism is grown in a nutrient medium containing known nutritional sources for actinomycetes, i.e., assimilable sources of carbon and nitrogen added with optional inorganic salts and other known growth factors. Submerged aerobic conditions are preferably employed for the production of large quantities of antibiotic, although surface cultures and bottles may also be used for production of limited amounts. The general procedures used for the cultivation of other actinomycetes are applicable to the present invention.

The nutrient medium should contain an appropriate assimilable carbon source, such as ribose, glucose, sucrose, and cellobiose. As a nitrogen source, ammonium chloride, ammonium sulfate, urea, ammonium nitrate, sodium nitrate, etc., may be used either alone or in combination with organic nitrogen sources, such as peptone, meat extract, yeast extract, corn steep liquor, soybean meal, cotton seed meal, etc. There may also be added, if necessary, nutrient inorganic salts to provide sources of sodium, potassium, calcium, ammonium, phosphate, sulfate, chloride, bromide, carbonate, zinc, magnesium, manganese, cobalt, iron, and the like.

When Strain R103-3 is cultivated in a nutrient medium supplemented with a source of D-serine, the novel antibiotic pradimicin FL, as well as known pradimicins FA-1 and FA-2, are produced. In addition, pradimicins A, C, and L are also co-produced. It has been discovered, unexpectedly, that Strain R103-3 is an efficient producer of pradimicins FA-1 and FA-2 under these conditions. For the production of pradimicins FL and FA-1 and FA-2, either D-serine or DL-serine may be used.

Production of the antibiotic complex comprising pradimicin components may be effected at any temperature suitable for satisfactory growth of the producing organism, e.g., 25°–40° C., and is most conveniently carried out at a temperature of around 27°–32° C. Ordinarily, optimum antibiotic production is obtained by flask fermentation after shaking with incubation periods of 5 to 12 days. If fermentation is to be carried out in tank fermentors, it is desirable to use a vegetative inoculum in a nutrient broth from a slant culture or a lyophilized culture. After obtaining an active inoculum in this manner, it is aseptically transferred to the fermentation medium in a tank fermentor. Antibiotic production in tank fermentors usually reached a maximum after 3–15 days of incubation. Agitation in the tank fermentor is provided by stirring, and aeration may be achieved by injection of air or oxygen into the agitated mixture. Antibiotic production may be monitored by HPLC followed with spectroscopic techniques, or by a conventional biological assay.

Pradimicin L and pradimicin FL thus produced may be recovered from the fermentation broth by any suitable methods for such recovery; examples of these methods include extraction, precipitation, chromatography, and other art recognized conventional techniques. A preferred isolation and purification sequence for pradimicins L and FL is given in Examples 2 and 5, respectively.

It is to be understood that, for the production of pradimicins L and FL, the present invention is not limited to the particular organism mentioned above but includes the use of variants and mutants thereof that retain the antibiotic-producing capability. Such variants and mutants can be produced from parent strains by various means, such as X-ray radiation, UV-radiation, and chemical mutagens, such as N-methyl-N'-nitro-N-nitrosoguanidine. One such mutant strain is strain A10019 (ATCC No. 55091) obtained from strain R103-3 by mutation with NTG as previously described. A10019 may be cultured to produce pradimicin antibiotic complex containing pradimicin L, under conditions substantially the same as those for strain R103-3.

Thus, another aspect of the present invention provides a method for producing pradimicins A, B, C, D, E and L which comprises cultivating an antibiotic-producing strain of *Actinomadura verrucosospora* subsp. *neohibisca* under submerged and aerobic conditions in a medium containing assimilable carbon and nitrogen sources, recovering from the medium an antibiotic complex comprising said pradimicins, and separating the desired pradimicin compound from said antibiotic complex. Preferably, the antibiotic-producing strains are strains R103-3, ATCC No. 53930, and A10019, ATCC No. 55091. Preferably, the method is used to produce pradimicin L.

A further aspect of the invention provides a method for producing pradimicins FA-1, FA-2 and FL which comprises cultivating an antibiotic-producing strain of *Actinomadura verrucosospora* subsp. *neohibisca* under submerged and aerobic conditions in a medium containing assimilable carbon and nitrogen sources, and a source of D-serine, recovering from the medium an antibiotic complex comprising said pradimicins, and separating the desired pradimicin compound from said antibiotic complex. Preferably, the antibiotic-producing strain is strain R103-3, ATCC No. 53930. Strain R103-3 when cultivated in a medium containing a source of D-serine produces pradimicins FA-1/FA-2 more efficiently than the previously known producers which are various strains of *Actinomadura hibisca*, for example ATCC No. 53815 and ATCC No. 53816; thus, the present method provides an improved method for producing pradimicins FA-1/FA-2. Another preferred embodiment of the present invention provides a method for producing pradimicin FL.

2. Preparation of N-alkyl Derivatives

The secondary sugar group of pradimicin L and pradimcin FL may be converted to a tertiary amino group by reductive alkylation which comprises first reacting the antibiotic starting material with an aldehyde or a ketone to form an imine and subsequently reducing the imine thus formed. The condensation and reduction may be conducted in the same reaction vessel in one step or in two separate steps. The carbonyl reactant may be an aldehyde or a ketone having 1 to 5 carbon atoms, but preferably 1 to 3 carbon atomes, for example, formaldehyde, acetaldehyde, propionaldehyde, and acetone. Reduction of the imine may be accomplished by using reducing agents such as metal hydrides, for example, sodium borohydride, sodium cyanoborohydride, and lithium aluminum hydride. The reaction is carried out in a polar organic solvent or a mixture thereof, such as water, acetonitrile, lower alkanols, and dimethyl sulfoxide. The reaction temperature is not particularly restricted and may be from about 20° to about 100° C.; in general the reaction may be conveniently carried out at ambient temperature. In our experience, the reductive alkylation carried out at room temperature is usually complete within 1–4 days. Pradimicins having a tertiary amino sugar generally exhibit higher water solubility than the parent compounds.

BIOLOGICAL ACTIVITY

Representative compounds of the present invention were tested in vitro against various fungi by serial agar dilution method in either Sabouraud dextrose agar or yeast morphology agar containing 1/15 M phosphate buffer. Thus, approximately 0.003 ml of fungal suspension containing $10^6$–$10^7$ cells/ml was applied to the surface of agar plates containing the test antibiotic. The minimum inhibitory concentration (MIC) values for the test compounds were recorded after the cultures had been incubated for 40–60 hours at 28° C. The results are provided in Tables 4a, 4b, and 4c.

TABLE 4a

In vitro Antifungal Activity of Pradimicin L and N-Methyl Pradimicin L

| Test Organism | MIC ($\mu$g/ml) | | |
|---|---|---|---|
| | Pradimicin L | N-Methyl Pradimicin L | Pradimicin A |
| Candida albicans IAM4888 | 6.3 | 12.5 | 6.3 |
| C. albicans A9540 | 12.5 | 12.5 | 100.0 |
| Cryptococcus neoformans D49 | 0.8 | 6.3 | 1.6 |
| C. neoformans IAM4514 | 0.8 | 6.3 | 1.6 |
| Aspergillus fumigatus IAM2530 | 3.1 | 6.3 | 1.6 |
| A. fumigatus IAM2034 | 3.1 | 6.3 | 3.1 |
| A. flavus FA21436 | 100.0 | >100.0 | >100.0 |
| Fusarium moniliforme A2284 | 6.3 | 12.5 | 6.3 |
| Trichophyton mentagrophytes D155 | 6.3 | 25.0 | 1.6 |
| T. mentagrophytes #4329 | 12.5 | 25.0 | 6.3 |
| Blastomyces dermatitidis D40 | 3.1 | 6.3 | 6.3 |
| Sporothrix schenckii IF08158 | 0.8 | 1.6 | 1.6 |
| Petriellidium boydii IF08078 | 25.0 | 25.0 | 6.3 |
| Mucor spinosus IF05317 | >100.0 | >100.0 | >100.0 |

Medium: Sabouraud dextrose agar
Inoculuin: $10^6$ CFU/ml

TABLE 4b

In vitro Antifungal Activity of Pradimicin FL and Pradimicin L

| Test Organism[2] | MIC ($\mu$g/ml)[1] | | |
|---|---|---|---|
| | Pradimicin FL | Pradimicin L | Pradimicin A |
| Saccharomyces cerevisiae ATCC 9763 | 3.1 | 6.3 | 6.3 |
| Candida albicans A9540 | 6.3 | 25.0 | 12.5 |
| Candida albicans ATCC 32354 (B311) | 6.3 | 6.3 | 6.3 |
| Candida albicans 83-2-14 (Juntendo) | 6.3 | 100.0 | 12.5 |
| Candida albicans ATCC 38247 (polyene-R) | 3.1 | 3.1 | 6.3 |
| Candida tropicalis 85-8 (Kitasato) | 6.3 | >100.0 | 12.5 |
| Candida tropicalis IAN 10241 | 6.3 | 100.0 | >100.0 |
| Cryptococcus neoformans D49 | 3.1 | 1.6 | 1.6 |
| Cryrtococcus neoformans IAM 4514 | 1.6 | 0.8 | 1.6 |
| Aspergillus fumigatus IAM 2034 | 3.1 | 3.1 | 1.6 |
| Trichophyton mentagrophytes #4329 | 3.1 | 3.1 | 3.1 |

[1]Determined after incubation for 40 hours at 28° C. (*Trichophyton mentagrophytes:* 60 hours, 28° C.).
[2]Inoculum size $10^6$ cells/ml (*Trichophyton mentagrophytes:* $10^7$ cells/ml) in yeast morphology agar containing 1/15 M phosphate buffer.

TABLE 4c

In vitro Antifungal Activity of N-Methyl Pradimicin FL

| Test Organism[2] | MIC (µg/ml)[1] N-Methyl Pradimicin FL |
|---|---|
| *Saccharomyces cerevisiae* ATCC 9763 | 3.1 |
| *Candida albicans* A9540 | 6.3 |
| *Candida albicans* ATCC 32354 (B311) | 6.3 |
| *Candida albicans* 83-2-14 (Juntendo) | 6.3 |
| *Candida tropicalis* 85-8 (Kitasato) | 12.5 |
| *Candida tropicalis* IAM 10241 | 12.5 |
| *Cryptococcus neoformans* D49 | 6.3 |
| *Cryptococcus neoformans* IAM 4514 | 6.3 |
| *Aspergillus fumigatus* IAM 2034 | 6.3 |
| *Trichophyton mentagrophytes* #4329 | 6.3 |

[1]·Determined after incubation for 40 hours at 28° C. (*Trichophyton mentaprophytes*: 60 hours, 28° C.).
[2]·Inoculum size $10^6$ cells/ml (*Trichophyton mentagrophytes*: $10^7$ cells/ml) in yeast morphology agar containing 1/15 M phosphate buffer.

As can be seen from the data in Tables 4a–4c, antibiotics of the present invention are active against a variety of yeasts and fungi. Thus, the antibiotics of the present invention are useful medicaments for treating an animal host, including humans afflicted with a yeast or fungal infection.

For treatment of fungal infections in animals and human beings, the antibiotics of the present invention may be given in an antifungally effective amount by any accepted routes of administration; these include, but are not limited to, intravenous, intramuscular, oral, intranasal, and for superficial infections, topical administration. Preferably, the antibiotic is given systemically. Preparations for parenteral administration include sterile aqueous or non-aqueous solutions, suspensions, or emulsions. They may also be manufactured in the form of sterile solid compositions which can be dissolved in sterile water, physiological saline, or some other sterile injectable medium immediately before use. Oral formulation may be in the form of tablets, gelatin capsules, powders, lozenges, syrups, and the like. For topical administration, the compound may be incorporated into lotions, ointments, gels, creams, salves, tinctures, and the like. Unit dosage forms may be prepared using methods generally known to those skilled in the art of pharmaceutical formulations.

It will be appreciated that, when treating a host infected with a fungus susceptible to the antibiotics of this invention, the actual preferred route of administration and dosage used will be at the discretion of the attending clinician skilled in the treatment of fungal infections and will vary according to the particular antibiotic selected, the causative organism, its sensitivity to the antibiotic, severity and site of the infection, and patient characteristics, such as age, body weight, rate of excretion, concurrent medications, and general physical condition.

The following examples are illustrative without limiting the scope of the present invention.

EXAMPLE 1

Production of Pradimicin L by Fermentation of *Actinomadura verrucosospora* subsp. *neohibisca* Strain R103-3

A. Agar Slant

*Actinomadura verrucosospora* subsp. *neohibisca* strain R103-3 (ATCC No. 53930) was propagated on an agar slant of modified Bennett's medium at 28° C. for 14 days. The composition of the medium is soluble starch (Nichiden Kagaku) 0.5%, glucose 0.5%, fish meat extract (Mikuni Kagaku Sangyo) 0.1%, yeast extract (Oriental Yeast) 0.1%, NZ-case (Sheffield) 0.2%, NaCl 0.2%, $CaCO_3$ 0.1%, and agar 1.6%.

B. Seed Culture

A small portion of the microbial growth from the slant culture was inoculated to a 500-ml Erlenmeyer flask containing 100 ml of the vegetative medium consisting of soluble starch (Nichiden Kagaku) 1%, glycerol 1%, yeast extract (Oriental Yeast) 1%, peptone (Daigo Eiyo) 0.5%, NaCl 0.3%, and $CaCO_3$ 0.2%. The pH of the medium was adjusted to 7.0 before autoclaving. The seed culture was incubated at 28° C. for 7 days on a rotary shaker at 200 rpm.

C. Flask Fermentation

A 5 ml portion of the seed culture was transferred to a 500-ml Erlenmeyer flask containing 100 ml of the production medium (FR-17) consisting of soluble starch (Nichiden Kagaku) 1%, glucose 1%, sodium L-glutamate 0.1%, L-methionine 0.05%, L-arginine 0.05%, $(NH_4)_2SO_4$ 0.1%, $MgSO_4.7H_2O$ 0.05%, NaCl 0.05%, $CaCO_3$ 0.3%, $K_2HPO_4$ 0.6%, and salt solution 1% (v/v) ($FeSO_4.7H_2O$ 0.1 g, $ZnSO_4.7H_2O$ 0.1 g, and $MnCl_2.4H_2O$ 0.1 g in 1 liter of water). The pH of the medium was adjusted to 7.0 before autoclaving. The fermentation was carried out at 28° C. for 14 days on a rotary shaker (200 rpm). Antibiotic production in the fermentation broth was determined spectrophotometrically. The production of total pradimicin reached a maximum at 290 µg/ml on day 11. The ratio of the different components produced is as follows:

| Total Production* (µg/ml) | Ratio (%) of Pradimicin** | | | | | |
|---|---|---|---|---|---|---|
| | A | B | C | D | E | L |
| 290 | 58 | 6 | 22 | 2 | 1 | 11 |

*Determination of pradimicin components. The fermentation broth was centrifuged at 10,000 rpm for 10 minutes. The supernatant was diluted with 0.01N NaOH—MeOH (1:1) and its optical density measured at 500 nm. Antibiotic concentration was expressed as amount of pradimicin A free base. Data from the fermentation broths of 11 days.
**Determined by HPLC (Waters M600, YMC-A301-3 system) using a 3:1 mixture of 0.15% potassium phosphate-buffer acetonitrile (pH 3.5) as solvent, with UV detection at 254 nm.

EXAMPLE 2

Isolation and Purification of Pradimicin L

The fermentation broth (10.0 L) was centrifuged to remove the mycelial mass. The supernatant was acidified to pH 4.1 using 6N HCl and kept at 5° C. for 2 hours. The dark-red precipitate was collected by filtration and then dissolved in 900 ml of water adjusted to pH 9.1 with 6N NaOH. The solution was filtered to remove insoluble impurities, and the filtrate was adjusted to pH 2.0 and then applied onto a column of Diaion HP-20 (800 ml). The column was washed with water (3.0 L) and eluted with 60% aqueous acetone (pH 2.5). The acetone was removed in vacuo, and the red residue was washed with ethyl acetate (400 ml) and then dried to afford a complex of pradimicins as their hydrochloride salts (4.5 g). The complex solid (4.5 g) was dissolved in 450 ml of a mixture of $CH_3CN$-0.15% $KH_2PO_4$, pH 3.5 (22:78), and subjected to reversed phase column chromatography on ODS-A60 (10 L, Yamamura Chemical Lab.) which had been equilibrated with the same solvent mixture. Elution was carried out with the above solvent mixture, and the eluate was fractionated. The fractions were analyzed by HPLC (Column: YMC A-301-3, 4.6 mm I.D.×100 mm, 3 μ, ODS, Yamamura Chemical Lab., Mobile phase: $CH_3CN$-0.15% $KH_2PO_4$, pH 3.5 (25:75), Flow rate: 0.8 ml/minute, Detection: UV absorption at 254 nm, Retention time: pradimicin L 10.76 minutes). The fractions containing pradimicin L were pooled and concentrated in vacuo to remove acetonitrile. The concentrate was desalted by Diaion HP-20 chromatography to yield semi-pure pradimicin L hydrochloride (563 mg). The powder (50 mg) was dissolved in 24% acetonitrile/phosphate buffer (pH 3.5) and chromatographed on an ODS column (RP-18, 2.2 L, Merck Ltd.) eluted with the same solvent. The fractions containing the desired compound were combined and concentrated in vacuo to remove acetonitrile. The concentrate was passed through a Diaion HP-20 column (0.2 L). The column was washed with water (0.6 L) and eluted with 60% aqueous acetone (pH 3.0). The eluates were dried to afford 24 mg of pure pradimicin L hydrochloride as an orange powder (purity by HPLC: 99%). In order to convert the hydrochloride salt to its free form and to remove contaminated inorganic salts, an aqueous solution (3 ml) of the salt (12 mg) was adjusted to pH 5.6 with 0.1N NaOH to deposit pure zwitterionic form of pradimicin L (5.0 mg).

Physico-Chemical Properties of Pradimicin L

Form: Dark Red Amorphous Powder

Solubility: Soluble in dimethyl sulfoxide, dimethylformamide, and acidic or alkaline water; slightly soluble in ethanol, methanol, and water.

MP: >200° C. (dec.).

$[\alpha]_D^{27}$: +415° (C=0.1, 0.1N HCl).

SIMS: m/z 871 (M+H)+.

UV $\lambda_{max}$ nm (ε)

in 0.01N HCl-MeOH (1:1): 234 (33,400), 298 (28,900), 460 (12,000)

in 0.01N NaOH-MeOH (1:1): 241 (32,700), 319 (14,500), 498 (13,900).

IR (KBr) $cm^{-1}$: 3380, 2900, 1620–1600, 1385, 1295, 1260, 1160, 1060.

$^1$H NMR (400 MHz, DMSO-$d_6$) δ: 1.31 (3H, d, J=6.8), 1.37 (3H, d, J=7.3), 2.35 (3H, s), 2.75 (3H, s), 3.10 (1H, t, J=9.0), 3.17 (1H, t-like, J=9.0), 3.21–3.26 (2H, m), 3.49 (1H, dd, J=6.4, 11.5), 3.53–3.58 (2H, m), 3.76 (1H, dd, J=1.7, 11.5), 3.93 (1H, qui, J=6.8), 3.97 (3H, s), 3.99 (1H, m), 4.46 (1H, qui, J=7.3), 4.50 (1H, d, J=7.7), 4.61 (1H, d, J=9.8), 4.65 (1H, d, J=9.8), 4.79 (1H, d, J=7.7), 5.79* (1H, br-s), 5.85* (1H, br-s), 6.91 (1H, d, J=2.6), 7.13 (1H, br-s), 7.31 (1H, d, J=2.6), 8.02 (1H, s), 8.20* (1H, br-s), 8.30* (1H, br-s), 8.38* (1H, d, J=6.8), 12.83* (1H, s).

*Disappeared in $D_2O$ addition.

EXAMPLE 3

Production of Pradimicin L by Fermentation of Strain A10019 (ATCC No. 55091)

The mutant strain A10019 was grown in a 500-ml Erlenmeyer flask containing 100 ml of seed medium having the same composition as the one given in Example 1 B for 7 days at 32° C. on a rotary shaker at 200 rpm. Five ml of the seed culture was inoculated into a 500-ml Erlenmeyer flask containing 100 ml of production medium having the same composition as the one given in Example 1 C. The fermentation was carried out at 28° C. for 8 days on a rotary shaker at 200 rpm. The production of the total pradimicin was at 345 μg/ml. The ratio of antibiotic components was 34.1% for pradimicin L, 7.5% for pradimicin C, and 42.4% for pradimicin A.

EXAMPLE 4

Production of Pradimicin FL by Fermentation of *Actinomadura verrucosospora* subsp. *neohibisca* Strain R103-3

A 5 ml portion of the seed culture, as prepared in Example 1 B, was transferred to a 500-ml Erlenmeyer flask containing 100 ml of the production medium consisting of soluble starch (Nichiden Kagaku) 1%, glucose 1%, sodium L-glutamate 0.1%, L-methionine 0.05%, L-arginine 0.05%, $(NH_4)_2SO_4$ 0.1%, $MgSO_4 \cdot 7H_2O$ 0.05%, NaCl 0.05%, $CaCO_3$ 0.3%, $K_2HPO_4$ 0.6%, salt solution 1% (v/v) ($FeSO_4 \cdot 7H_2O$ 0.1 g and $MnCl_2 \cdot 4H_2O$ 0.1 g in 1 liter of water), and DL-serine 0.5% (or D-serine 0.25%). The pH of the medium was adjusted to 7.0 before autoclaving. The fermentation was carried out at 28° C. for 10 days on a rotary shaker (200 rpm). Antibiotic production in the fermentation broth was spectrophotometrically determined. The production of total pradimicin reached a maximum at 330 μg/ml on day 10. Pradimicin A, C, FA-1, FA-2, and L were also co-produced. The content of pradimicin FL was estimated to be approximately 4.8% of the total production by HPLC analysis.

EXAMPLE 5

Isolation and Purification of Pradimicn FL

The harvested broth (20 L, 200 flasks) was centrifuged and the mycelial cake was discarded. The supernatant (20 L) was extracted with 20 L of a mixture of n-butanol-methanol (15:5) at pH 2.4. The solvent extract was transferred to 3 L of alkaline water adjusted to pH 9.0 with 1N-NaOH. The solution was adjusted to pH 3.5 and applied on a column of Diaion HP-20 (2.3 L). The column was washed with water (10 L) and eluted with 60% aqueous acetone (pH 2.5). Fractions containing the desired product were pooled, concentrated in vacuo, and then dried to yield a dark-red solid which was a complex of pradimicins as their hydrochloride salts (7.2 g). The complex (6.8 g) was dissolved in 340 ml of water, and the solution was filtered to remove insoluble impurities. The filtrate was washed with 150 ml of ethyl acetate (3 times) and dried to afford a partially purified complex. The residue was dissolved in 500 ml of a mixture of $CH_3CN$-0.15% $KH_2PO_4$, pH 3.5 (22:78), and subjected to reversed-phase chromatography on a column of ODS-A60 (10 L, Yamamura Chemical Lab.) which had been equilibrated with the same solvent mixture. Elution was carried out with the above solvent mixture, and the eluate was collected in 0.5 L fractions. The fractions were analyzed by HPLC (Column: YMC gel A-301-3, 4.6 mm I.D.×100 mm, 3 μm, ODS, Yamamura Chemical Lab., Mobile phase: $CH_3CN$-0.15% $KH_2PO_4$, pH 3.5 (25:75), Flow rate: 0.8 ml/minute, Detection: UV absorption at 254 nm, Retention time: pradimicin FL 5.41 minutes). The fractions containing pradimicin FL were pooled (2.8 L) and concentrated in vacuo to remove acetonitrile. The concentrate was desalted by Diaion HP-20 chromatography (50 ml) to yield semi-pure pradimicin FL hydrochloride (40 mg). The powder (24 mg) was dissolved in acetonitrile/0.15% phosphate buffer, pH 3.5 (22:78, 2.5 ml), and chromatographed on an ODS column (ODS-A60, 40 ml) eluted with the same solvent. The fractions containing the desired compound were combined (100 ml) and concentrated in vacuo to remove acetonitrile. The concentrate was passed through a Diaion HP-20 column (20 ml). The column was washed with water (100 ml) and eluted with 60% aqueous acetone (pH 3.0). The eluates were dried to afford 19.5 mg of pure pradimicin FL hydrochloride as an orange powder (purity by HPLC: 99%).

Physico-Chemical Properties of Pradimicin FL

Form: Orange Amorphous Powder

MP: >200° C. (dec.).

FAB-MS (Negative) m/z: 886 (M).

UV $\lambda_{max}$ nm ($\epsilon$)

in 0.01N HCl-MeOH (1:1): 234 (31,900), 299 (27,800), 459 (10,600)

in 0.01N NaOH—MeOH (1:1): 242 (34,500), 319 (15,200), 497 (13,600).

IR (KBr) cm$^{-1}$: 3400, 2940, 1720, 1630–1610, 1390, 1335, 1295, 1260, 1160, 1080–1060.

$^1$H NMR (400 MHz, DMSO-d$_6$) δ: 1.29 (3H, d, J=6.8), 2.34 (3H, s), 2.71 (3H, s), 3.05 (1H, t, J=9.0), 3.16 (1H, t, J=7.7), 3.18–3.23 (2H, m), 3.41–3.53 (3H, m), 3.71–3.80 (3H, m), 3.92 (1H, qui, J=7.7), 3.93–3.97 (1H, m), 3.95 (3H, s), 4.44–4.49 (1H, m) 4.47 (1H, d, J=6.8), 4.55–4.63 (2H, m), 4.80 (1H, d, J=8.1), 5.90* (2H, br-s), 6.90 (1H, s), 7.04 (1H, s), 7.25 (1H, d, J=2.1), 7.92 (1H, s), 8.20* (1H, br-s), 8.34* (1H, br-s), 8.42* (1H, d-like), 12.95* (1H, s).

*Disappeared in D$_2$O addition.

EXAMPLE 6

Production of Pradimicin FA-1 and FA-2 by Fermentation of *Actinomadura verrucosospora* subsp. *neohibisca*

A. Agar Slant

*Actinomadura verrucosospora* subsp. *neohibisca* strain R103-3 (ATCC No. 53930) was propagated on an agar slant of modified Bennett's medium containing soluble starch 0.5%, fish meat extract 0.1%, yeast extract 0.1%, NZ-case (Scheffield) 0.2%, NaCl 0.2%, CaCO$_3$ 0.1%, and agar 1.6% and was incubated at 28° C. for 10 days.

B. Seed Culture

A small portion of the microbial growth from the slant culture was inoculated to a 500-ml Erlenmeyer flask containing 100 ml of a seed medium composed of soluble starch 1%, glucose 1%, yeast extract 0.5%, peptone 0.5%, NaCl 0.3%, and CaCO$_3$ 0.2%. The pH of the medium was adjusted to 7.0 before autoclaving, and the culture was incubated at 32° C. for 6 days on a rotary shaker.

C. Flask Fermentation

A 5 ml portion of the seed culture thus obtained was transferred to another 500-ml Erlenmeyer flask which contains 100 ml of the fermentation medium composed of glucose 3%, Protein S (soybean flour, Ajinomoto) 3%, CaCO$_3$ 0.3%, and DL-serine 0.5%. The fermentation was carried out at 28° C. for 11 days on a rotary shaker. The total antibiotic activity in the fermentation broth was determined by the broth dilution method using *Candida albicans* A9540 as the indicator organism in Sabouraud dextrose broth. The UV assay at 500 nm in 0.01N NaOH—MeOH (1:1) solution was also used in parallel with the above bioassay. Pradimicin A hydrochloride (Lot 18-11-5, 1,000 μg/ml $E_{1\ cm}^{1\%}$ =180) was used as the standard sample for both microbiological and UV assays. Determination of each component was carried out by a HPLC using Microsorb Short One C$_{18}$ column (Rainin Instrument Co.) eluting with acetonitrile-0.15% KH$_2$PO4 (adjusted to pH 3.5 with H$_3$PO$_4$) (7:17). The ratio of each pradimicin component was pradimicin FA-1:FA-2:A:C (62:1:36:1). An example of the time course and the production ratio of pradimicin FA-1 and FA-2 is shown as follows:

|  | Day 7 | Day 9 | Day 11 |
|---|---|---|---|
| Total Potency (μg/ml) | 1,470 | 1,870 | 1,600 |
| FA-1 + FA-2 (%) | 63 | 62 | 63 |

D. Tank Fermentation

Twenty (20) L of well-grown seed culture was transferred to 100 L of the production medium in a tank fermentor. The composition of the production medium is the same as that for flask fermentation. The tank fermentor was operated at 32° C. for 10 days under agitation at 250 rpm with 120 L/minute of aeration. The total antibiotic potency reached a maximum on the 9th day at 520 μg/ml.

EXAMPLE 7

Isolation of Pradimicins FA-1 and FA-2

Fermentation broth of Example 6 was harvested and centrifuged to remove the mycelial mass. The supernatant was adjusted to pH 2.0 with 6N HCl and centrifuged to remove the precipitate as impurities. The supernatant was adjusted to pH 5.5 with 6N NaOH, and the resultant precipitate was collected by filtration. The precipitate was dissolved in water at pH 10.0, and the solution was then adjusted to pH 2.0 with 6N HCl and then applied to Diaion HP-20 column (4.1 L). The column was washed with water and eluted with 0.001N HCl-acetone (40:60). Fractions containing pradimicins were collected (9.5 L) and concentrated in vacuo at 40° C., and the concentrate (400 ml) was lyophilized to give a reddish powder of pradimicin complex (29 g) having a purity of about 80%. The ratio of each component analyzed by HPLC was pradimicin FA-1 62.2%, pradimicin FA-2 0.7%, pradimicin A 36.4%, and pradimicin C 0.7%. This complex was separated into the individual components by reversed phase silica gel chromatography using ODS 60A column (Yamamura Chemical Lab.) and, as eluant, acetonitrile-0.15% KH$_2$PO$_4$ (adjusted to pH 3.5 with 1N-H$_3$PO$_4$) (22:78 v/v). Each active fraction was concentrated and desalted with Diaion HP-20 and lyophilized.

EXAMPLE 8

Preparation of N-Methyl Pradimicin L (II, R$^1$=CH$_3$, R$^2$=CH$_3$)

Pradimicin L (18 mg) was dissolved in 1.8 ml of water, and the solution was adjusted to pH 7.8 with addition of 0.1N sodium hydroxide and diluted with 1.8 ml of acetonitrile. Subsequently, aqueous formaldehyde (>35%, 0.12 ml) and sodium cyanoborohydride (18 mg) were added to the solution at room temperature. The solution was allowed to stand for 48 hours at room temperature, and the progress of reaction was monitored by HPLC. The organic solvent was evaporated in vacuo, and the aqueous solution was diluted with 30 ml of water. The solution was applied on a column of Diaion HP-20 (5 ml). The column was washed with 30 ml of water and eluted with 10 ml of 60% aqueous acetone (pH 3.0). Concentration of the dark-red eluate afforded amorphous solid of N,N-dimethyl pradimicin L hydrochloride (18 mg).

MP: >180° C. (dec.).

IR (KBr) cm$^{-1}$: 3400, 1730, 1620, 1450, 1380, 1335, 1295, 1255, 1160, 1130, 1070.

UV $\lambda_{max}$ (in 0.01N NaOH-50% MeOH) nm ($\epsilon$): 211 (30,600), 319 (11,600), 501 (11,100).

$^1$H NMR (400 MHz, DMSO-d$_6$) δ: 3.02 (6H, br-s, N(CH$_3$)$_2$).

FAB-MS (m/z): 885 (M+H)$^+$.

EXAMPLE 9

Preparation of N-Methyl Pradimicin FL (II, R$^1$=CH$_2$OH, R$^2$=CH$_3$)

Pradimicin FL hydrochloride (37 mg) was dissolved in 4 ml of water, and the solution was adjusted to pH 8.0 by addition of 0.1N sodium hydroxide and diluted with 4 ml of acetonitrile. Subsequently, aqueous formaldehyde (>35%, 0.3 ml) and sodium cyanoborohydride (45 mg) were added to the solution at room temperature. The reaction mixture was allowed to stand for 66 hours at room temperature, and the reaction progress was monitored by HPLC. The reaction mixture was evaporated in vacuo. The residue was dissolved in 10 ml of water and subjected to reversed-phase chromatography on ODS column (RP-18, 2.2 L, Merck Ltd.) which was equilibrated with a mixture of CH$_3$CN-0.15% KH$_2$PO$_4$, pH 3.5 (25:75) before use. Elution was carried out with the same solvent mixture. The fractions containing the desired compound were combined (2.7 L) and concentrated in vacuo to remove CH$_3$CN. The concentrate (2.2 L) was passed through a Diaion HP-20 column (50 ml). The column was washed with water (300 ml) and eluted with 60% aqueous acetone (pH 3.0). The eluates (50 ml) were concentrated and dried to afford 17 mg of homogeneous N,N-dimethyl pradimicin FL hydrochloride. The purity of this compound was estimated at 99% by HPLC.

MP: >180° C. (dec.).

IR (KBr) cm$^{-1}$: 3400, 2950, 1730, 1630–1610, 1450, 1390, 1340, 1300, 1260, 1070.

UV λ$_{max}$ (in 0.01N NaOH-50% MeOH) nm (ε): 243 (32,800), 320 (14,500), 498 (13,300).

$^1$H NMR (400 MHz, DMSO-d$_6$) δ: 3.01 (6H, S, N(CH$_3$)$_2$).

FAB(+)-MS (m/z): 901 (M+1).

EXAMPLE 10

Preparation of N-ethyl Pradimicin L (II, R$^1$=CH$_3$, R$^2$=CH$_2$CH$_3$)

The general procedure of Example 8 is followed with the exception that acetaldehyde is used in place of formaldehyde to provide the title compound.

EXAMPLE 11

Preparation of N-propyl Pradimicin L (II, R$^1$=CH$_3$, R$^2$=(CH$_2$)$_2$CH$_3$)

The general procedure of Example 8 is followed with the exception that propionaldehyde is used in place of formaldehyde to provide the title compound.

EXAMPLE 12

Preparation of N-isopropyl Pradimicin L (II, R$^1$=CH$_3$, R$^2$=CH(CH$_3$)$_2$)

The general procedure of Example 8 is followed with the exception that acetone is used in place of formaldehyde to provide the title compound.

EXAMPLE 13

Preparation of N-ethyl Pradimicin FL (II, R$^1$=CH$_2$OH, R$^2$=CH$_2$CH$_3$)

The general procedure of Example 9 is followed with the exception that acetaldehyde is used in place of formaldehyde to provide the title compound.

EXAMPLE 14

Preparation of N-propyl Pradimicin FL (II, R$^1$=CH$_2$OH, R$^2$=(CH$_2$)$_2$CH$_3$)

The general procedure of Example 9 is followed with the exception that propionaldehyde is used in place of formaldehyde to provide the title compound.

EXAMPLE 15

Preparation of Pradimicin L by Chemical Synthesis

A. Preparation of Pradimicin B

A mixture of pradimicin A sodium salt (6 g, 7 mmol), acetic acid (240 ml), and 2N HCl (240 ml) was stirred at 80° C. for 7 hours. The solvent was then evaporated and the residual oil dissolved in water. The solution was absorbed on μBondapak C$_{18}$ column (400 ml), and the column was washed with water and eluted with 25% aqueous acetonitrile (adjusted to pH 3.5 with 1N HCl). Fractions containing the desired product were collected and evaporated to give pradimicin B (3.25 g, 62% yield, purity 85% by HPLC). This product was used in the following benzyloxycarbonylation without further purifications.

MP: 140° C.

IR υ$_{max}$ (KBr) cm$^{-1}$: 3400, 1720, 1600.

UV λ$_{max}$(0.01N-NaOH) nm (E$_{1cm}^{1\%}$): 319 (189), 498 (183).

$^1$H NMR (DMSO-d$_6$) δ: 1.27 (3H, d, J=6.4 Hz, 5'-Me), 1.33 (3H, d, J=7.3 Hz, 17-Me), 2.31 (3H, s, 3-Me), 2.69 (3H, s, 4'-NMe), 3.88 (1H, q, 5'-H), 4.40 (1H, dq, J$_{17,NH}$=7.3 Hz, 17-H), ca. 4.5–4.6 (2H, m, 5- and 6-H), 4.70 (1H, m, 1'-H), 6.96 (1H, d, J$_{10,12}$=2.6 Hz, 10-H), 7.18 (1H, s, 4-H), 7.31 (1H, d, 12-H), 8.08 (1H, brs, 7-H).

B. Preparation of 4'-N-benzyloxycarbonylpradimicin B

A mixture of pradimicin B (3.13 g, 4.2 mmol) and N,O-bis(trimethylsilyl)acetamide (20.8 ml, 84 mmol) in dry methylene chloride (150 ml) was stirred at ambient temperature for about 0.5 hour until a solution was obtained. Benzyloxycarbonyl chloride (3.0 ml, 21 mmol) was added to the above solution, and stirring was continued for 2.5 hours. The solvent was evaporated, and to the oily residue was added methanol (210 ml) and 1N HCl (42 ml), successively, under ice-water cooling. The mixture was stirred at ambient temperature for 0.5 hour, and then the solvent was evaporated. The residue was triturated with water, filtered, and washed with water and ether, successively, to yield a solid (3.32 g, yield 94%), which consisted of the title compound (65%) and its methyl ester (19%). This sample was used for the next reaction without further purifications. A part of this sample (120 mg) was purified by C$_{18}$ column using 50% aqueous acetonitrile (pH 3.5 with 1N-HCl) as eluent to afford the title compound (47 mg, 90% pure by HPLC).

MP: 215° C. (dec.).

IR$_{υmax}$ (KBr) cm$^{-1}$: 3370, 1720, 1660, 1600.

UV$_{λmax}^{(MeOH)}$ nm (E$_{1cm}^{1\%}$): 234 (251), 291 (221), 469 (95).

$^1$H NMR (DMSO-d$_6$-D$_2$O) δ: 1.02 & 1.04 (3H, each d, J=6.4 Hz, 5'-Me), 1.32 (3H, d, J=7.3 Hz, 17-Me), 2.29 & 2.30 (3H, each s, 3-Me), 3.08 & 3.13 (3H, each s, 4'-NMe), 3.96 (3H, s, 11-OMe), 4.39 (1H, q, 17-H), 4.46 (1H, brd, J$_{5,6}$=10.3 Hz, 5-H), 4.54 (1H, brd, 6-H), 4.60 (1H, d, J$_{1',2'}$=7.3 Hz, 1'-H), 5.06 & 5.10 (2H, each ABq, J=12.8 Hz, —CH$_2$Ph), 6.95 (1H, d, J$_{10,12}$=2.1 Hz, 10-H), 7.09 (1H, brs, 4-H), 7.30 (1H, d, 12-H), ca. 7.4 (5H, m, Ph), 8.08 (1H, brs, 7-H).

FAB(+)-MS (m/z): 843 (M+H).

C. Preparation of 4'-N-benzyloxycarbonylpradimicin B methyl ester

Thionyl chloride (1.4 ml) and 4'-N-benzyloxycarbonyl-pradimicin B were added to a cold mixture of methanol (100 ml) and dry 1,2-dichloroethane (30 ml), and the mixture was stirred at ambient temperature for 3 hours. The solvents were removed, and the residue was purified by silica gel (Wakogel C-200, 450 g in CHCl₃) column with CHCl₃—CH₃OH (15:1, v/v) as eluent to give the title compound (2.80 g in 86% yield) as deep red powder, 95% pure by HPLC.

MP: 200°–205° C. (dec.).

IR$_{\upsilon max}$ (KBr) cm$^{-1}$: 3400, 1730, 1670, 1620, 1440.

UV$_{\lambda max}^{(MeOH)}$ nm (E$_{1cm}^{1\%}$): 226 (285), 280 (245), 500 (118).

$^1$H NMR (DMSO-d$_6$-D$_2$O) δ: 1.03 & 1.04 (3H, each d, J=6.9 Hz, 5'-Me), 1.32 (3H, d, J=7.3 Hz, 17-Me), 2.26 & 2.27 (3H, each s, 3-Me), 3.08 & 3.13 (3H, each s, 4'-NMe), 3.66 (3H, s, COOMe), 3.73 (1H, m, 5'-H), 3.93 (3H, s, 11-OMe), 4.44 (1H, q, 17-H), 4.50 (1H, d, J$_{5,6}$=10.9 Hz, 5-H), 4.61 (1H, d, J$_{1',2'}$=7.6 Hz, 1'-H), [5.00 & 5.12 (1H, ABq, J=12.9 Hz) and 5.10 (1H, s), —CH$_2$Ph], 6.88 (1H, brs, 10-H), 7.04 (1H, s, 4-H), 7.25 (1H, brs, 12-H), ca. 7.4 (5H, m, Ph), 7.98 (1H, S, 7-H).

FAB(+)-MS (m/z): 857 (M+H), 879 (M+Na).

D. Preparation of Pradimicin L

To a stirred suspension of 4'-N-benzyloxycarbonyl-pradimicin B methyl ester (1.03 g, 1.2 mmol), mercuric cyanide (2.43 g, 9.2 mmol), mercuric bromide (1.08 g, 3 mmol), and molecular sieves 3A (12 g) in dry 1,2-dichloroethane (240 ml) was added tetra-O-acetyl-α-D-glucopyranosyl bromide (1.48 g, 3 mmol), and the mixture was heated at 90° C. (bath temperature) with stirring. After 15, 21, and 84 hours, a set of mercuric cyanide (2.43 g), mercuric bromide (1.08 g), and tetra-O-acetylglucosyl bromide (2, 1.48 g) were added, and the mixture was heated for a total of 103 hours. The insolubles were filtered off and washed with chloroform; the combined filtrates were washed with 10% aqueous NaHCO₃, water and brine, dried over Na₂SO₄, and evaporated in vacuo. The residual oil (5.97 g) was chromatographed on a silica gel (Wakogel C-200, 100 g in toluene) column using toluene, toluene-ethyl acetate (2:1), and chloroform-methanol (10:1) as eluants. The chloroform-methanol eluates were combined and evaporated. The residue (2.70 g) was separated by a column of silica gel (Wakogel C-200, 100 g in CHCl₃), eluting with chloroform-methanol (100:1, 50:1, 25:1, and 10:1) to give 2 fractions of coupling products, fraction A (Rf 0.35 on tlc, CHCl₃:MeOH=25:1; deep-red powder, 283 mg) and fraction B (Rf 0.52, orange powder, 2.03 g).

To a solution of fraction A (270 mg) in methanol (27 ml) was added 1N-NaOH (6 ml), and the mixture was stirred at ambient temperature for 1 hour. The mixture was adjusted to pH 6.5 with 1N-HCl, diluted with water (100 ml), and evaporated to remove the organic solvent. The aqueous solution was placed on a column of Diaion HP-20 (50 ml), and the column was washed with water and eluted with 40% aqueous acetonitrile to afford a crude fraction containing 4'-N-CBZ-pradimicin L (224 mg), which was further purified by a reversed phase column (Waters, μBondapak C$_{18}$, 55–105μ, 400 ml), eluting with 45% aqueous acetonitrile (pH 3.5 with 1N HCl) to yield the semi-pure 4'-N-CBZ-pradimicin L (57 mg), purity 75% on HPLC [Retention time 9.4 minutes; A/B=40/60]. A mixture of 4'-N-CBZ-pradimicin L obtained above (50 mg) and 10% Pd-C (20 mg) in methanol (20 ml) and water (4 ml) was hydrogenated for 2 hours. The catalyst was removed, the filtrate evaporated, and the residue purified on a reversed-phase column (Waters, μBondapak C$_{18}$, 80 ml) with 20–25% aqueous acetonitrile (pH 3.5 with 1N HCl) as eluants to give pradimicin L (12 mg, yield 1.1%, purity by HPLC 85%) as a deep-red powder.

MP: 155° C. (dec.).

IR $_{\upsilon max}$ (KBr) cm$^{-1}$ 1720, 1600, 1510.

UV$_{\lambda max}^{(0.01N-NaOH)}$ nm (E$_{1cm}^{1\%}$) 216 (231), 232 (228), 320 (106), 500 (106).

$^1$H NMR (DMSO-d$_6$) δ: 1.28 (3H, d, J=6.8 Hz, 5'-CH$_3$), 1.33 (3H, d, J=7.7 Hz, 17-CH$_3$), 2.31 (3H, s, 3-CH$_3$), 2.72 (3H, brs, 4'-NCH$_3$), 3.96 (3H, s, 11-OCH$_3$), 4.40 (H, quintet, J=7.3 Hz, 17-H), 4.48 (1H, d, J=7.3 Hz, 1"-H), 4.61 (2H, brs, 5-H and 6-H), 4.80 (1H, brd, 1'-H), 6.96 (1H, d, J=2.6 Hz, 10-H), 7.11 (1H, s, OH), 7.14 (1H, s, 4-H), 7.31 (1H, d, J=2.6 Hz, 12-H), 7.36 (1H, s, OH), 8.05 (1H, s, 7-H).

FAB(+)-MS (m/z): 873 (M+3H).

EXAMPLE 16

Preparation of N-isopropyl pradimicin FL (II, R$^1$= CH$_2$OH. R$^2$=CH(CH$_3$)$_2$)

The general procedure of Example 9 is followed with the exception that acetone is used in place of formaldehyde to provide the title compound.

What is claimed is:

1. A compound having the formula

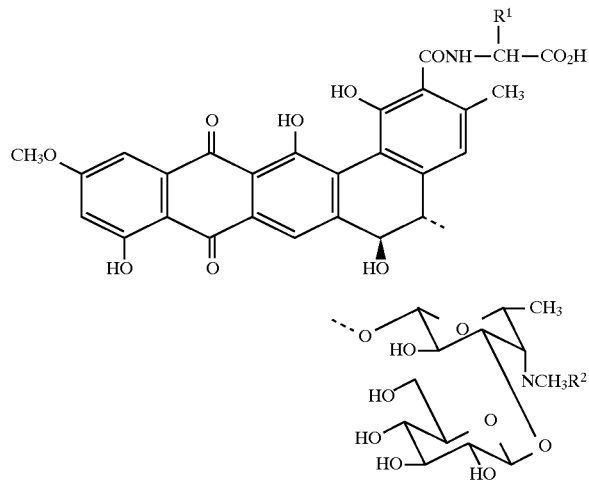

wherein

R$^1$ is methyl or hydroxymethyl, and the resulting amino acid residue has the D-configuration; and R$^2$ is hydrogen or C$_{1-5}$ alkyl; provided that when R$^1$ is methyl, R$^2$ cannot be hydrogen;

or a pharmaceutically acceptable salt thereof.

2. A compound of claim 1 wherein R$^2$ is C$_{1-5}$ alkyl.
3. A compound of claim 1 wherein R$^2$ is methyl.
4. A compound of claim 1 wherein R$^1$ is methyl.
5. A compound of claim 1 wherein R$^1$ is hydroxymethyl.
6. A compound of claim 4 wherein R$^2$ is methyl.
7. A compound of claim 5 wherein R$^2$ is hydrogen.
8. A compound of claim 5 wherein R$^2$ is methyl.
9. A pharmaceutical composition which comprises an antifungal effective amount of a compound of claim 1 and a pharmaceutically acceptable vehicle.

10. An isolated compound having the formula
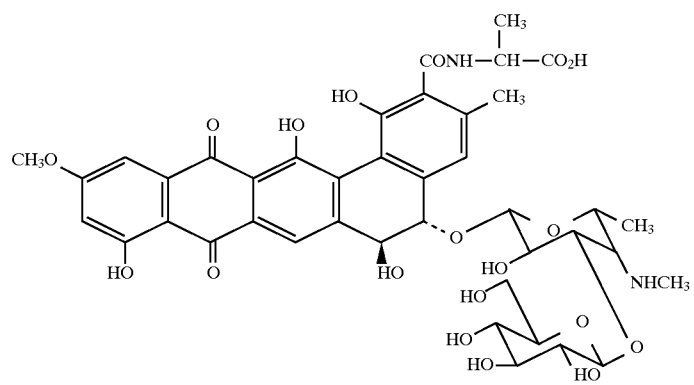
or a pharmaceutically acceptable salt thereof.
* * * * *